United States Patent [19]

Bayles et al.

[11] Patent Number: 4,925,863

[45] Date of Patent: May 15, 1990

[54] ANTIFUGAL AZOLE COMPOUNDS

[75] Inventors: Richard W. Bayles, Bramhall; Francis T. Boyle, Congleton; Michael B. Gravestock, Bramhall; James M. Wapdleworth, Chelford, all of United Kingdom

[73] Assignee: Imperial Chemical Industries PLC, London, England

[21] Appl. No.: 156,017

[22] Filed: Feb. 16, 1988

Related U.S. Application Data

[62] Division of Ser. No. 768,838, Aug. 23, 1985.

[30] Foreign Application Priority Data

Sep. 5, 1984 [GB] United Kingdom ............... 8422414
Sep. 5, 1984 [GB] United Kingdom ............... 8422415
Mar. 28, 1985 [GB] United Kingdom ............... 8508111

[51] Int. Cl.$^5$ ............... C07D 249/08; A61K 31/41; A01N 43/653
[52] U.S. Cl. ............... 514/383; 548/266.6
[58] Field of Search ............... 548/262; 514/383

[56] References Cited

U.S. PATENT DOCUMENTS 4,549,900 10/1985 Kramer et al. ............... 548/262
4,625,036 11/1986 Boyle ............... 548/262

FOREIGN PATENT DOCUMENTS 044605 1/1982 European Pat. Off. ............ 548/262

Primary Examiner—Richard L. Raymond
Assistant Examiner—Patricia L. Morris
Attorney, Agent, or Firm—Cushman, Darby & Cushman

[57] ABSTRACT 1,3-Diazolyl-2-propanol derivatives of the formula

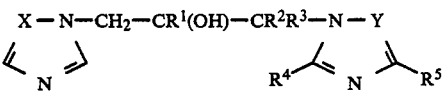

wherein X and Y are N or CH, $R^1$ is phenyl, heterocyclyl, heterocyclyl-alkyl, -alkenyl or -alkynyl, optionally substituted, $R^2$ and $R^3$ are hydrogen or alkyl, and $R^4$ and $R^5$ are hydrogen, amino, alkoxyalkyl, aminoalkyl, alkylaminoalkyl, dialkylaminoalkyl, or alkenyl, or phenyl, phenylalkyl or phenylalkenyl, heterocycyl, heterocyclyalkyl or heterocyclylalkenyl, each optionally substituted, provided that when $R^1$ is optionally substituted phenyl at least one of $R^1$, $R^4$ and R5 is, or contains, a phenyl ring bearing at least one substitutent selected from cyano, cyanoalkyl, nitro, aminocarbonylalkyl, halogeneoalkoxy and radicals of the formulae —$CONR^6R^7$, —$NHCOR^8$ or $OR^9$ as defined herein, and the acid addition salts of compounds which contain a basic substituent; together with processes for their manufacture, pharmaceutical, veterinary and plant antifungal compositions, a method of treating fungal diseases in plants, and the use of the compounds for the manufacture of pharmacuetical or veterinary antifungal compositions.

7 Claims, No Drawings

ANTIFUGAL AZOLE COMPOUNDS

This is a division of application Ser. No. 768,838, filed Aug. 23, 1985.

This invention relates to novel antifungal azoles, and in particular it relates to 1,3-di-azolyl-2-propanol derivatives, to a process for preparing them, to pharmaceutical, veterinary and plant antifungal and plant growth regulating compositions containing them, to processes for controlling fungal infections of plants and to processes for regulating plant growth.

European Patent Application Number 81302146.6 discloses azolylpropanol derivatives of the formula I wherein R is alkyl, cycloalkyl, aryl or aralkyl, any of which may be optionally substituted, and $A^1$ and $A^2$ are imidazolyl or 1,2,4-triazol-1-yl radicals, and their acid addition salts, metal complexes, ethers and esters, and describes the use of such compounds as pharmaceutical and agricultural antifungals, and as plant growth regulators.

United Kingdom Patent Application Number 2,099,818A describes particularly the compound of the formula I wherein R is a 2,4-difluorophenyl radical, and its pharmaceutical and veterinary antifungal utility.

According to the present invention there is provided a compound of the formula II wherein X and Y, which may be the same or different, are each a methylidyne or nitrilo radical;

$R^1$ is a phenyl radical, which may optionally bear one or more substituents selected from:

halogen, 1-6C alkyl, alkoxy, halogenoalkyl, halogenoalkoxy, alkylamino and alkylsulphonyl radicals, di(1-6C alkyl)amino, heterocyclyl(1-6C)alkyl, cyano, cyano (1-6C)alkyl, nitro and 2-6C aminocarbonylalkyl radicals;

radicals of the formula —$CONR^6R^7$, wherein $R^6$ and $R^7$, which may be the same or different, are each hydrogen or a formyl, 1-6C alkyl or halogenoalkyl, 2-6C alkanoyl or alkoxycarbonyl, 3-8 cycloalkyl, 3-8C cycloalkyl(1-4C alkyl), aryl, aryl(1-4C alkyl), aroyl, heteroaryl or heteroaryl(1-4C alkyl) radical, provided that $R^6$ and $R^7$ are not both hydrogen; or $NR^6R^7$ may be a morpholino, pyrrolidinyl, piperidino or 4-(2-6C alkanoyl)piperazino radical;

radicals of the formula —$NHCOR^8$, wherein $R^8$ is hydrogen or a 1-6C alkyl or halogenoalkyl, 3-8C cycloalkyl, 3-8C cycloalkyl(1-4C alkyl), aryl, aryl(1-4C alkyl), heteroaryl or heteroaryl(1-4C alkyl) radical; and radicals of the formula —$OR^9$ wherein $R^9$ is a 3-8C cycloalkyl, 2-6C alkenyl, alkynyl or aminocarbonylalkyl, cyano(1-6C alkyl), 1-6C alkoxy(1-6C alkyl), 1-6C halogenoalkoxy(1-6C alkyl), 1-6C alkanoyl(1-6C alkyl), aryl, aryl(1-4C alkyl), aroyl(1-6C alkyl), heteroaryl and heteroaryl(1-4C alkyl) radicals;

or $R^1$ is a heterocyclyl, heterocyclyl(1-6C)alkyl, heterocyclyl(2-6C)alkenyl or heterocyclyl(2-6C) alkynyl radical, in each of which the heterocyclyl part is a 5- or 6-membered aromatic ring containing 1 or 2 heteroatoms selected from nitrogen, oxygen and sulphurand in each of which the heterocyclyl ring may bear one or more substituents selected from those given above as phenyl substituents in the definition of $R^1$;

$R^2$ and $R^3$, which may be the same or different are each hydrogen or a 1-6C alkyl radical;

and $R^4$ and $R^5$, which may be the same or different, are each hydrogen or an amino or 1-6C alkyl radical; an alkoxyalkyl, aminoalkyl, alkylaminoalkyl, dialkylaminoalkyl or alkenyl radical wherein each alkyl, alkoxy or alkenyl part is of 1-6 carbon atoms; a phenyl, phenyl(1-6C)alkyl, phenoxy(1-6C)alkyl or phenyl(2-6C)alkenyl radical in each of which the phenyl ring may optionally bear one or more substituents selected from those given above as phenyl substituents in the definition of $R^1$; a heterocyclyl, heterocyclyl(1-6C)alkyl or heterocyclyl(2-6C)alkenyl radical, in each of which the heterocycyl part is a 5- or 6-membered aromatic ring containing 1 or 2 heteroatoms selected from nitrogen, oxygen and sulphur, and in each of which the heterocyclyl ring may bear one or more substituents selected from those given above as phenyl substituents in the definition of $R^1$; or a radical of the formula III in which $R^{10}$ and $R^{11}$ are each hydrogen or a 1-6C alkyl radical and $R^{12}$ is a phenyl radical bearing one or more substituents selected from cyano, cyano(1-6C)alkyl, nitro and 2-6C aminocarbonylalkyl radicals, and radicals of the formulae —$CONR^6R^7$, —$NHCOR^8$ and —$OR^9$ as defined above;

provided that, when $R^1$ is an optionally substituted phenyl radical, at least one of $R^1$, $R^4$ and $R^5$ is, or contains, a phenyl ring bearing at least one substituent selected from cyano, cyano(1-6C)alkyl, nitro, 2-6C aminocarbonylalkyl, 1-6C halogenoalkoxy and radicals of the formulae —$CONR^6R^7$, —$NHCOR^8$ and —$OR^9$ as defined above, and the acid addition salts of those compounds which contain a basic substituent.

Preferably, X and Y are each a nitrilo radical, so that the azole rings are each 1,2,4-triazol-1-yl radicals.

A suitable value for $R^4$ or $R^5$, when either of them is a phenyl(1-6C)alkyl radical is, for example, a benzyl, phenethyl, alpha-methylphenethyl, 1-phenylethyl or 3-phenylpropyl radical.

A suitable optional substituent in $R^1$ when it is an optionally substituted phenyl radical, or in $R^4$ or $R^5$ when either is an optionally-substituted phenyl, phenyl(1-6C)alkyl, phenoxy(1-6C)-alkyl or phenyl(2-6C)alkenyl radical is, for example, a fluorine, chlorine, bromine or iodine atom, a methyl, propyl, hexyl, methoxy, tert-butoxy, hexyloxy, trichloromethyl, difluoromethyl, trifluoromethyl or 2,2,2-trifluoroethyl radical, a fluoromethoxy, difluoro-methoxy, trifluoromethoxy, 2-fluoroethoxy, 2,2-difluoro-ethoxy, 2,2,2-trifluoroethoxy, 1,1,2-trifluoroethoxy, 2,2,3,3-tetrafluoropropoxy or 1-methyl-2,2,2-trifluoroethoxy radical, a methylamino, hexylamino, dimethylamino or diethylamino radical, a mesyl radical, or a morpholino(1-6C)alkyl, piperidino(1-6C)alkyl, 1-pyrrolidinyl(1-6C)alkyl, 4-(1-6C alkyl)piperazinyl(1-6C)alkyl or 4-(2-6C alkanoyl)-piperazinyl(1-6C)alkyl radical. Up to five such optional substituents may be present, but mono- and di-substituted such radicals are preferred.

A suitable value for a cyano(1-6C)alkyl substituent in $R^1$, $R^4$, $R^5$ or $R^{12}$, or for $R^9$ when it is such a radical is, for example, a cyanomethyl, 2-cyanoethyl, 1-cyano-1-methylethyl or 1- or 6-cyanohexyl radical.

A suitable value for a 2-6C aminocarbonylalkyl substituent in $R^1$, $R^4$, $R^5$ or $R^{12}$, or for $R^9$ when it is such a radical, is, for example, an aminocarbonylmethyl, 1- or 2-aminocarbonylethyl, 1-aminocarbonyl-1-methylethyl, 1-, 2- or 3-aminocarbonylpropyl or 6-aminocarbonylhexyl radical.

A suitable value for $R^6$, $R^7$, or $R^8$ when any is a halogenoalkyl radical is, for example, a chloroalkyl or fluoroalkyl radical, for example a chloromethyl, trichloromethyl, difluoromethyl, trifluoromethyl, 2,2,2-trifluoroethyl, 3,3,3-trifluoropropyl, 2,2,3,3,3-pentafluoropropyl or 6-chlorohexyl radical.

A suitable value for $R^6$ or $R^7$, when either is a 2–6C alkanoyl radical is, for example, an acetyl, propionyl, butyryl, isobutyryl, valeryl, isovaleryl, pivaloyl or hexanoyl radical.

A suitable value for $R^6$ or $R^7$, when either is a 2–6C alkoxycarbonyl radical is, for example, a methoxycarbonyl, ethoxycarbonyl, propoxycarbonyl or hexyloxycarbonyl radical.

A suitable value for $R^6$, or $R^7$, $R^8$ or $R^9$, when any is a 3–8C cycloalkyl radical is, for example, a cyclopropyl, cyclopentyl, cyclohexyl or cyclooctyl radical.

A suitable value for $R^6$, $R^7$ or $R^8$, when either is a 3–8C cycloalkyl(1–4C alkyl) radical is, for example, a cyclopropylmethyl, 4-cyclopropylbutyl, cyclooctylmethyl or 4-cyclooctylbutyl radical.

A suitable value for $R^6$, $R^7$, $R^8$ or $R^9$, when any is an aryl radical, is, for example, a phenyl or naphthyl radical, optionally substituted, for example by one or more halogen atoms or 1–3C alkyl, alkoxy or halogenoalkyl radicals.

A suitable value for $R^6$, $R^7$, $R^8$ or $R^9$, when any is an aryl(1–4C alkyl) radical is, for example, a benzyl, phenethyl, 1-phenylethyl, 1-, 2- or 3-phenylpropyl or 4-phenylbutyl radical, optionally substituted in the phenyl ring thereof by one or more halogen atoms or 1–3C alkyl, alkoxy or halogenoalkyl radicals.

A suitable value for $R^6$ or $R^7$, when either is an aroyl radical, is, for example a benzoyl or alpha- or beta-naphthoyl radical, optionally substituted by one or more halogen atoms or 1–3C alkyl, alkoxy or halogenoalkyl radicals.

A suitable value for $R^6$, $R^7$, $R^8$ or $R^9$ when either is a heteroaryl radical, is, for example, a 2-, 3- or 4-pyridyl or 2-pyrimidinyl radical, optionally substituted by one or more halogen atoms or 1–3C alkyl, alkoxy or halogenoalkyl radicals.

A suitable value for $R^6$, $R^7$, $R^8$ or $R^9$ when any is a heteroaryl(1–4C alkyl) radical is, for example, a 2-, 3- or 4-pyridylmethyl radical, similarly optionally substituted.

A suitable value for $R^9$ when it is a 2–6C alkenyl radical is, for example, a vinyl, allyl, 1-propenyl, 2,4-butadienyl or 5-hexenyl radical.

A suitable value for $R^9$ when it is a 2–6C alkynyl radical, is, for example, an ethynyl, 1- or 2-propynyl or 5-hexynyl radical.

A suitable value for $R^9$ when it is a 1–6C alkoxy(1–6C alkyl) radical is, for example, a methoxymethyl, ethoxymethyl, 2-methoxyethyl, 2-ethoxyethyl, hexyloxymethyl, 1- or 6-methoxyhexyl, or 1- or 6-hexyloxyhexyl radical.

A suitable value for $R^9$ when it is a 1–6C alkanoyl(1–6C alkyl) radical is, for example, a 2-oxopropyl, 2-oxobutyl or 7-oxododecyl radical.

A suitable value for $R^9$ when it is an aroyl(1–6C alkyl) radical is, for example, a benzoylmethyl, 2-benzoylethyl or 6-benzoylhexyl radical, optionally substituted in the benzene ring thereof by one or more halogen atoms or 1–3C alkyl, alkoxy or halogenoalkyl radicals.

In $R^1$, $R^4$ or $R^5$ a suitable value for the heterocyclyl radical, or for the heterocyclyl part of a heterocyclylalkyl, heterocyclylalkenyl or heterocyclylalkynyl radical is for example, a 2-, 3- or 4-pyridyl, 2-pyrazinyl, 3- or 4-pyridazinyl, 2-, 4- or 5-pyrimidinyl, 2- or 3-furyl, 2- or 3-thienyl, quinolyl, quinazolinyl, quinoxalinyl, cinnolinyl, phthalazinyl or naphthyridinyl radical, especially a 2-pyridyl or 3-thienyl radical. The alkyl part of a heterocyclyalkyl radical is preferably of 1 to 6 carbon atoms, and the alkenyl or alkynyl part of a heterocyclylalkenyl or heterocyclylalkynyl radical is preferably of 2 to 6 carbon atoms.

Preferred optional substituents in the heterocyclyl part of $R^1$ are halogen atoms, particularly chlorine atoms, and 1–6C alkyl, alkoxy, halogenoalkyl and halogenoalkoxy radicals. Up to three such substituents may be present, but monosubstituted radicals are preferred.

Preferred values for $R^1$ are therefore 5-halogenopyrid-2-yl, 5-trifluoromethylpyrid-2-yl and 5-halogenothien-2-yl radicals.

A suitable value for $R^2$, $R^3$, $R^4$, $R^5$, $R^6$, $R^7$, $R^8$, $R^{10}$ or $R^{11}$, when any is a 1–6C alkyl radical or for the 1–6C alkyl part of a substituent in $R^1$, $R^4$ or $R^5$ is, for example, a methyl, ethyl, propyl, isopropyl, butyl, isobutyl, sec-butyl, tert-butyl, pentyl, neopentyl or hexyl radical.

A suitable value for $R^4$ or $R^5$, when either of them is an alkoxyalkyl, aminoalkyl, alkylaminoalkyl, dialkylaminoalkyl or alkenyl radical wherein each alkyl, alkoxy or alkenyl part contains up to 6 carbon atoms, is for example, a methoxymethyl, 6-methoxyhexyl, hexyloxymethyl, aminomethyl, 6-aminohexyl, methylaminomethyl, 6-methylaminohexyl, hexylaminomethyl, dimethylaminomethyl, 6-dimethylaminohexyl, dihexylaminomethyl, vinyl, allyl, 1-hexenyl or 5-hexenyl radical.

A suitable value for $R^4$ or $R^5$ when either is a phenoxy-(1–6C)-alkyl or phenyl-(2–6C)-alkenyl radical is, for example, a phenoxymethyl, styryl, alpha-methylstyryl or cinnamyl radical.

It will be understood that, since the carbon atom bearng substituents $R^1$ and hydroxy is asymmetrically substituted, and the carbon atom bearing substituents $R^2$ and $R^3$, and various substituent groups, may also be asymmetrically substituted, the compounds of the invention will exist in racemic, meso or optically-active forms. It is common general knowledge in the art how such forms may be separated and isolated, and their antifungal properties determined.

Suitable acid addition salts of compound of the formula II which contain a basic substituent are, for example, the hydrochloride, nitrate, sulphate, acetate, and phosphate.

A preferred group of compounds of the invention comprises compounds of the formula II wherein $R^4$ is hydrogen and $R^5$ is a substituent, other than hydrogen, as defined above.

A further preferred group of compounds of the invention comprises compounds of the formula II wherein X and Y are both nitrilo radicals, $R^1$ is a fluorophenyl radical, $R^2$, $R^3$ and $R^4$ are hydrogen, and $R^5$ is a styryl radical substituted in the phenyl ring by a cyano, 1–4C alkoxy bearing 1 to 4 fluorine substituents, (1–4C fluoroalkyl)pyridyloxy, N-(halogenophenyl)carbamoyl, (2–3C alkoxycarbonyl)-(1–4C)alkyl or N-(1–4C alkyl)-N-(1–4C-fluoroalkyl)carbamoyl radical.

Particular such compounds are those wherein X and Y are both nitrilo radicals, $R^1$ is 2,4-difluorophenyl, $R^2$, $R^3$ and $R^4$ are each hydrogen, and $R^5$ is a 4-(difluoromethoxy)styryl, trifluoromethoxystyryl, 4-(2,2,2-trifluoroethoxy)-styryl, 4-(1,1,2,2-tetrafluoro ethoxy)styryl, 4-(2,2,3,3-tetrafluoropropoxy)styryl, 4-(1-methyl-2,2,2-trifluoroethoxy)styryl, 4-(3-trifluoromethylpyrid-2-yl)styryl, 4-cyanostyryl, 4-(1-methoxycarbonylpropyl)styryl, 4-(4-chlorophenylcarbamoyl)styryl or 4-[N-methyl-N-(2,2,3,3,4,4,4-heptafluorobutyl)carbamoyl]styryl radical.

A further preferred group of compounds of the invention comprises compounds of the formula II wherein X and Y are both nitrilo radicals, $R^1$ is a halogenopyridyl radical, $R^2$, $R^3$ and $R^4$ are each hydrogen and $R^5$ is a styryl radical substituted in the phenyl ring by a cyano, a 1–4C alkyl or alkoxy radical bearing 1 to 7 fluorine substituents, (1–4C fluoroalkyl)pyridyloxy, N-(halogenophenyl)carbamoyl, (2–3C alkoxycarbonyl)-(1–4C) alkyl, or N-(1–4C alkyl)-N-(1–4C-fluoroalkyl)carbamoyl radical.

Particular such compounds are those wherein X and Y are both nitrilo radicals, $R^1$ is 5-chloropyrid-2-yl, $R^2$, $R^3$ and $R^4$ are each hydrogen and $R^5$ is a 4-(2,2,2-trifluoroethoxy)styryl, 4-cyanostyryl or 4-trifluoromethylstyryl radical.

The compounds of the formula II may be prepared by methods known generally for the manufacture of similar compounds. Thus, the following processes are provided as further features of this invention, wherein X, Y, $R^1$, $R^2$, $R^3$, $R^4$, $R^5$, $R^{11}$ and $R^{12}$ have the meanings defined above:

(a) the reaction of an epoxide of the formula IV either as such, or formed in situ, with an azole of the formula V in the presence of a base; or (b) the reaction of an epoxide of the formula VI either as such, or formed in situ, with an azole of the formula VII in the presence of a base; or (c) the reaction of a halogeno compound of the formula VIII wherein Z is a halogen, preferably bromine or iodine, with an azole of the formula V; or (d) the reaction of a halogeno compound of the formula IX wherein Z has the meaning stated above, with an azole of the formula VII; or (e) the reaction of a ketone of the formula X with a Grignard reagent, $R^1$MgHal, wherein Hal is a halogen, or with an aryl-lithium derivative or, when $R^1$ is a heteroaryl radical, with a heteroaryl lithium derivative, $R^1$Li; or (f) the reaction of a ketone of the formula XI or XII with a Wittig reagent of the formula XIII or XIV respectively, wherein Q is a triphenylphosphine halide (Hal$^-$.Ph$_3$P$^+$—) or trialkyl phosphite ($R^{13}$O)$_2$PO—, (wherein $R^{13}$ is 1–6C lower alkyl) radical, which Wittig reagent may be preformed or formed in situ; or (g) for those compounds wherein $R^4$ or $R^5$ is a phenyl (2–6C)alkenyl radical, the reaction of a carbonyl compound of the formula XV wherein one of $R^{15}$ and $R^{16}$ is a radical of the formula —$COR^{10}$, and the other has any of the values defined above for $R^4$ or $R^5$, with a Wittig reagent of the formula XVI wherein Q has the meaning defined above, which Wittig reagent may be preformed or formed in situ; or (h) for those compounds wherein $R^1$ or $R^{12}$ is a phenyl radical substituted by a radical of the formula —$CONR^6R^7$, the reaction of a corresponding compound wherein $R^1$ or $R^{12}$ is a phenyl radical substituted by a carboxy radical, or of a reactive derivative thereof, for example an acid halide, anhydride or ester thereof, with an amino compound of the formula $NHR^6R^7$; or (i) for those compounds wherein $R^1$ or $R^{12}$ is a phenyl radical substituted by a radical of the formula —NHCOR$^8$, the reaction of a corresponding compound wherein $R^1$ or $R^{12}$ is a phenyl radical substituted by an amino radical, with an acid of the formula $R^8$.COOH or with a reactive derivative thereof, for example an acid halide, anhydride or ester thereof; or (j) for those compounds wherein $R^1$ or $R^{12}$ is a phenyl radical substituted by a radical of the formula —$OR^9$, the reaction of the corresponding compound of the formula II wherein $R^1$ or $R^{12}$ is a phenyl radical substituted by a hydroxy radical, with an alkylating agent of the formula $R^9R^{14}$, wherein $R^9$ has the meaning defined above and $R^{14}$ is a leaving group.

The epoxide of the formula IV, wherein Y is nitrilo, used as starting material in the above process, may be obtained by reacting a nitrile $R^{17}$CN (XVII) wherein $R^{17}$ has any of the meanings given above for $R^4$ or $R^5$, other than hydrogen, with for example ethanol in the presence of an acid to form an imido-ester XVIII, which is then reacted with formohydrazide, NH$_2$.NH.CHO, to form a triazole XIX. The triazole XIX is then reacted with an alpha-bromoketone XX, obtained by bromination of a ketone XXI, to form a mixture of azolyl ketones XI (one of $R^4$ and $R^5$=$R^{17}$, the other=hydrogen) which on reaction with dimethyl sulphonium methylide or dimethyl oxosulphonium methylide provides a triazole epoxide starting material of the formula IV.

The epoxide of the formula IV, wherein Y is methylidyne, may be prepared by the reaction of a Grignard reagent, $R^1$MgI, with ethyl cyanoacetate (XXII) to form a beta-keto-ester XXIII. The beta-keto-ester XXIII is reacted with sodium nitrite to form the oxime XXIV which is reduced to the corresponding amine XXV, and this amine is cyclised with an amide, $R^4$CONH$_2$, to form a substituted imidazole ester XXVI. This ester XXVI is then hydrolysed and decarboxylated to produce a substituted imidazole, XXVII, which is used in place of the triazole XIX in the reaction sequence described above, to form the epoxide IV (Y=methylidyne).

Alternatively, an epoxide IV wherein Y is methylidyne and $R^4$ is hydrogen may be manufactured by reacting methyl isocyanoacetate (XXVIII) with a nitrile, $R^5$CN, to form an imidazole ester (XXIX), which is then hydrolysed and decarboxylated, and the imidazole so obtained (XXX) is used in place of the triazole XIX in the reaction sequence described above, in order to obtain an epoxide IV wherein Y is methylidyne and $R^4$ is hydrogen.

The epoxide of the formula VI, used as starting material in the above process, may be obtained by brominating a methyl ketone XXXI, treating the bromoketone XXXII thus obtained with imidazole or 1,2,4-triazole in the presence of a base to form the triazole ketone XXXIII, and reacting the triazole ketone XXXIII with a Wittig reagent of the formula XXXIV, wherein Q has the meaning stated above. The olefin XXXV thus obtained is then epoxidised, for example with m-chloroperbenzoic acid, to form the required epoxide starting material VI.

Alternatively, the epoxide IV or the epoxide VI, when $R^2$ and $R^3$ are both hydrogen, may be formed in situ in the reaction from the corresponding ketone and dimethyl sulphonium iodide or dimethyl oxosulphonium iodide.

The halogeno compound of the formula IX, used as starting material in the above process, may be obtained by reacting an olefin XXXV with a hypohalous acid in conventional manner.

The halogeno compound of the formula VIII, used as starting material in the above process, may be obtained in a similar manner to IX, using an appropriate ketone in place of the methyl ketone XXXI, and reacting the bromo-ketone corresponding to XXXII with an appropriate substituted azole in place of imidazole or 1,2,4-triazole.

The ketones of the formulae X and XII, used as starting materials in the above process, may be manufactured by the same general process as described above for the manufacture of the ketone XI.

The Wittig reagents of the formula XIII and XIV, used as starting materials in the above process, may be manufactured by reacting 1-chloromethyl-1,2,4-triazole with either triphenylphosphine, as described in European Patent Publication No. 60222, or with potassium diethyl phosphite.

As indicated above, the compounds of the invention possess antifungal properties which make them useful in the treatment of candidosis and human dermatophyte infections.

This antifungal activity against *Candida albicans,* a causative fungus of candidosis, and *Trichophyton mentagrophytes,* var. quinkeanum, a causative fungus of ringworm, was demonstrated as follows:

Female mice of around 30 g. weight are injected sub-cutaneously on a Friday with 0.5 mg. of oestradiol benzoate. The following Monday (day 0) they are clipped on the back and then dosed orally with test compounds. They are then inoculated with *Candida albicans* in the vagina and *Trichophyton mentagrophytes* var. quinkeanum on the back, and then given a second dose of the same compound. Dosing is repeated once daily on days 1-4. On day 7 skin lesions are scored visually and vaginal samples taken for culture on agar. Groups of 5 mice are used and compounds are dosed initially at a level of 250 mg./kg. The dose is then reduced sequentially until a minimum effective dose (MED) is found. For example, the MED for the compound of Example 1 in this test was 0.25 mg/kg, the MED for the compound of Example 3 was 2.5 mg/kg., and the MED for compound of Example 4 was 1.0 mg/kg against Candida and no overt toxicity was seen at these MEDs.

Thus, according to a further feature of the invention there is provided a pharmaceutical or veterinary antifungal composition which comprises an antifungally effective amount of compound of the formula II together with a pharmaceutically or veterinarily acceptable diluent or carrier.

The composition of the invention may be in a conventional pharmaceutical form suitable for oral administration, for example a tablet, a capsule, an emulsion or an aqueous or oily solution or suspension, or suitable for topical application, for example a cream, ointment or gel. The composition may contain conventional pharmaceutical excipients, and may be manufactured by conventional pharmaceutical techniques.

Preferred pharmaceutical or veterinary compositions of the invention are compositions suitable for oral administration, and particularly tablets and capsules containing from 1 to 100, preferably 5 to 50 mg. of a compound of the invention.

The compounds of the invention also possess antifungal properties which are useful in combatting a wide variety of plant fungal diseases.

The compounds can move acropetally when applied to the plant tissue, and can also be volatile enough to be active in the vapour phase against fungi on the plant.

The compounds may be used as such for plant fungicidal purposes but are more conveniently formulated into compositions for such usage. The invention thus provides also a plant fungicidal composition comprising a compound of general formula II and a nonpharmaceutical carrier or diluent.

The invention also provides a method of combatting fungal diseases in a plant, which method comprises applying to the plant, to seed of the plant or to the locus of the plant or seed a compound of the formula II.

The compound can be applied in a number of ways, for example it can be applied, formulated or unformulated, directly to the foliage of a plant, to seeds or to the medium in which plants are growing or are to be planted, or it can be sprayed on, dusted on or applied as a cream or paste formulation, or it can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged, and the choice of a suitable conventional composition, and the method by which such a composition may be manufactured, are apparent to those skilled in the art.

The plant fungicidal compositions of this invention can comprise also other compound(s) having biological activity, e.g. compounds having similar or complementary fungicidal activity or compounds having plant growth regulating, herbicidal or insecticidal activity.

The invention is illustrated, but not limited, by the following Examples, in which temperatures are given in degrees Celsius.

EXAMPLE 1

A mixture of 3-(4-trifloromethoxystyryl)-1,2,4-triazole (12.0 g.), 2,4-difluoro-alpha-(1,2,4-triazol-1-yl)acetophenone (10.5 g.), trimethylsulphoxonium iodide (12.95 g.), potassium hydroxide (6.4 g.) and tert-butyl alcohol (200 ml.) was heated under reflux on a steam bath for 18 hours. The reaction mixture was evaporated to dryness and the residual gum was partitioned between ethyl acetate and water. The ethyl acetate layer was separated, washed with water, dried over magnesium sulphate and filtered and the solvent was evaporated to leave a brown gum. The gum was purified by gravity column chromatography on silica, using ethyl acetate as eluent. The resulting yellow gum was crystallised twice from ethyl acetate/hexane to give 1-(2,4-difluorophenyl)-2-[3-(4-trifluoromethoxystyryl)-1,2,4-triazol-1-yl]-1-(1,2,4-triazol-1-ylmethyl)ethanol, as a pale cream solid, m.p. 149°–151° C.

The 3-(4-trifuoromethoxystyryl)-1,2,4-triazole used as starting material in the above process, was obtained as follows:

4-Trifluoromethoxyaniline (29.0 g.) was added at 0° C. to concentrated hydrochloric acid (160 mls.) and the thick white suspension so obtained was cooled to −5° C. The suspension was diazotised by adding a solution of sodium nitrite (13.0 g.) in water (20 ml.) over 20 minutes, keeping the temperature below 0° C. After 2 hours at 0° C., the suspension was added portionwise to a solution of potassium iodide (40 g.) and iodine (60 g.) in water (260 ml.) at 10° C. and the solution was allowed to stand at room temperature for 1 hour. The dark solution so obtained was extracted with diethyl ether three times, and the combined ether extracts were washed sequentially with sodium sulphite, water and brine, and on evaporation gave a golden oil which was distilled under water pump pressure to give 4-trifluoromethoxyiodobenzene as a pale pink liquid, b.p. 107°–8° C.

A solution of 4-trifluoromethoxyiodobenzene (39.28 g.) in anhydrous diethyl ether (200 ml.) was added dropwise at −70° C. to n-butyl-lithium (96 ml. of a 1.6M solution in hexane) over 25 minutes. The solution was stirred for 30 minutes, and then dimethylformamide (14.83 g.) and anhydrous ether (50 ml.) were added over 15 minutes. After 1 hour, the solution was allowed to warm to −20° and was then hydrolysed by the addition of 3N hydrochloric acid (150 ml.). The organic layer was separated, and the aqueous layer was extracted twice with diethyl ether. The ether extracts were combined, washed with water, dried over magnesium sulphate and filtered, and the solvent was evaporated to give a yellow oil. Distillation of this oil gave 4-trifluoromethoxy benzaldehyde, b.p. 75°–7°/8 mm. of mercury, pressure.

Diethylcyanomethylphosphonate (24.22 g.) was added dropwise to a suspension of sodium hydride (3.28 g.) in dimethoxyethane (190 ml.) at or below 20° C. After gas evolution had ceased, 4-trifluoromethoxybenzaldehyde (26.0 g.) was added over 15 minutes, and after stirring for 40 minutes, the reaction mixture was poured into water (260 ml.), the organic layer was evaporated and the aqueous layer was extracted three times with diethyl ether. The ether extracts were combined, washed with water and dried over magnesium sulphate and the solvent was evaporated to give a yellow oil which crystallised after standing for several hours. On washing the solid with petroleum ether (b.p. 60°–80°), the solid was separated from the residual oil to give a product comprising 95% of the trans-form of 4-trifluoromethoxy-cinnamonitrile, n.m.r. in deuteriochloroform showed peaks at 5.86 ppm (1H, doublet), 7.1–7.67 pp. (5H, multiplet).

4-Trifluoromethoxycinnamonitrile (16.9 g.) was dissolved in a mixture of dry chloroform (50 ml.) and dry methanol (18 ml.). After cooling the solution to 0° C., a stream of hydrogen chloride was passed through the solution until saturation was achieved, then the solution was kept at 0°–5° C. in a refrigerator for four days. Evaporation of the solvents gave a pale yellow solid which was dissolved in absolute ethanol (90 ml.) and treated with formohydrazide (9.01 g.) and triethylamine (23.0 g.). The solution was heated on a steam bath for three and a half hours, then the solvents were evaporated and the residue was partitioned between ethyl acetate and water. The organic layer was separated, washed with water and dried over magnesium sulphate and the solvent was evaporated to give an orange oil, which was purified by column chromatography, using silica and chloroform/methanol (92:8 v/v) as the element, to give 3-(4-trifluoromethoxystyryl)-1,2,4-triazole, m.p. 125°–127° C.

EXAMPLE 2

A mixture of 4-trifluoromethoxy-alpha-(1,2,4-triazol-1-yl)-acetophenone (1.4 g.), 3-(4-trifluoromethylstyryl)-1,2,4-triazole (1.24 g.), trimethylsulphoxonium iodide (1.42 g.), potassium hydroxide (0.7 g.) and tert-butyl alcohol (30 ml.) was heated under reflux on a steam bath for four and half hours. The reaction mixture was poured into water and extracted three times with ethyl acetate. The extracts were combined, washed with water, dried over sodium sulphate and filtered, and the solvents were evaporated to give a brown gum. This gum was purified, firstly by column chromatography on silica, using ethyl acetate then ethyl acetate/methanol (9:1 v/v) as eluent, followed by medium pressure liquid chromatography using a Merck Lobar column, and chloroform/methanol (99.5:0.5 v/v), then chloroform/methanol (99:1.0 v/v) as eluent. Crystallisation of the resulting oil from diethyl ether gave 1-(4-trifluoromethoxyphenyl)-1-(1,2,4-triazol-1-ylmethyl)-2-[3-(4-trifluoromethylstyryl)-1,2,4-triazol-1-yl]ethanol, as a white solid, m.p. 193°–195° C.

The 4-trifluoromethoxy-alpha-(1,2,4-triazol-1-yl)-acetophenone used as starting material in the above process, may be obtained as follows:

A solution of 4-(trifluoromethoxy)iodobenzene (8.64 g.) in anhydrous diethyl ether (60 ml.) was added dropwise at −65° C. to n-butyl-lithium (21 ml. of a 1.6M solution in hexane) over 20 minutes. After stirring for a further 20 minutes, a solution of acetaldehyde (1.6 g.) in diethyl ether (15 ml.) was added, keeping the temperature below −60° C. Stirring was continued for 1 hour, after which time the temperature was allowed to rise to −30° C. and a mixture of glacial acetic acid (15 ml) and diethyl ether (20 ml.) was added. On reaching room temperature, the solution was poured into water, the organic layer was separated, washed with water and then sodium bicarbonate solution, dried over sodium sulphate and filtered, and the solvents were evaporated to give a pale yellow oil which was purified by column chromatography on silica and using chloroform, then chloroform/ethyl acetate (7:3 v/v) as eluent. Evaporation of the appropriate fractions gave a colourless oil which was dissolved in methylene dichloride (60 ml.) and treated with pyridinium chlorochromate (7.35 g.). After stirring for 3 hours, the reaction mixture was diluted with diethyl ether (100 ml.), and the suspension was filtered through a "Florosil" (trade mark) silica pad. Evaporation of the solvent gave 4-trifluoromethoxyacetophenone as a pale yellow oil. N.m.r. in deuteriochloroform gave signals at 2.59 (3H, singlet) and 7.7 (4H, quartet).

A solution of 4-trifluoromethoxyacetophenone (2.6 g.) in chloroform (50 ml.) was treated with a solution of bromine (2.04 g.) in chloroform (25 ml.) over 1 hour. After a further half hour, the reaction mixture was poured into water, the organic layer was separated, washed with water and dried over sodium sulphate, and the solvent was evaporated to a pale yellow oil which crystallised on standing. (3.4 g.). This solid was dissolved in acetonitrile (35 ml.), and sodium triazole (1.64 g.) was added. After stirring for one and a quarter hours, glacial acetic acid (3 ml.) was added, followed by water, and the resulting solution was extracted with ethyl acetate three times. The extracts were washed with water and dried over sodium sulphate, and the solvent was evaporated, to give a brown gum which was purified by chromatography on silica, using ethyl acetate as eluent. Evaporation of the appropriate fractions gave the required 4-trifluoromethoxy-alpha-(1,2,4-triazol-1-yl)acetophenone, m.p. 98°–101° C.

EXAMPLE 3

A mixture of 5-chloropyrid-2-yl(1,2,4-triazol-1-ylmethyl)ketone (1.8 g.), 3-(4-trifluoromethylstyryl)-1,2,4-triazole (1.94 g.), trimethylsulphoxoniumiodide (1.96 g.) and potassium hydroxide (0.91 g.) was heated in tert-butyl alcohol (15 ml.) for 24 hours at 75° C., cooled, and water (30 ml.) was added. The mixture was extracted with ethyl acetate (3×30 ml.), the organic extracts were combined and washed with water (2×50 ml.), and then dried over magnesium sulphate, filtered and evaporated to dryness. The residue was purified by medium pressure liquid chromatography using K60 silica with a gradient of 5% v/v ethanol/hexane, rising to 30% v/v ethanol/hexane, over the course of the separation (1 hour). Evaporation of the appropriate fractions gave 1-(5-chloropyrid-2-yl)-1-(1,2,4-triazol-1-ylmethyl)-2-[3-(4-trifluoromethylstyryl)-1,2,4-triazol-1-yl]ethanol, m.p. 159°-161° C.

The 3-(4-trifluoromethylstyryl)-1,2,4-triazole used as starting material in the above example may be prepared as follows:

4-Trifluoromethylcinnamonitrile (5 g.) was dissolved in a mixture of diethyl ether (10 ml.) and absolute ethanol (5 ml.) and stirred at 0°. Hydrogen chloride gas was passed into the solution for 1 hour and the resulting solution was allowed to stand at 5° for 48 hours.

The resulting white crystals were filtered and washed with ether to give a white solid which was redissolved in ethanol (50 ml.). This solution was treated successively with triethylamine (5 ml.) and a solution of formohydrazide (2 g.) in ethanol (15 ml.) and stirred at room temperature for 2 hours. The resulting solution was heated under reflux for 1 hour, then evaporated to dryness. The residue was partitioned between ethyl acetate and water, the ethyl acetate layer was then dried with anhydrous magnesium sulphate and filtered, and the filtrate was evaporated to dryness. The residual gum was heated at 120° for 1 hour then subjected to medium pressure chromatography on K60 silica, using chloroform as the eluting solvent, to give 3-(4-trifluoromethylstyryl)-1,2,4-triazole, m.p. 141°-143° C.

The 5-chloropyrid-2-yl-(1,2,4-triazol-1-yl-methyl)ketone used as the starting material in the above process may be prepared as follows:

5-Chloro-2-chloroacetylpyridine (20 g.) was dissolved in acetonitrile (25 ml.) and added dropwise to a refluxing solution of 1,2,4-triazole (6.2 g.) and potassium carbonate (13.4 g.) in acetonitrile (25 ml.). When the addition was complete, the solution was allowed to cool and was stirred for 2 hours. The solvent was evaporated and the residue was partitioned between ethyl acetate and water. The ethyl acetate layer was separated, washed twice with water and twice with brine, dried over sodium sulphate and filtered. The filtrate was evaporated to dryness under reduced pressure, and the residue was chromatographed on a K60 silica column, eluting with ethyl acetate, to give 5-chloropyrid-2-yl-1,2,4-triazol-1-ylmethyl ketone which after crystallisation from ethyl acetate/petroleum ether (b.p. 60°-80°), had m.p. 146°-148°.

EXAMPLE 4

Sodium hydride (55% oil dispersion) (0.4 g.) was added to a solution of 3-(4-cyanostyryl)-1,2,4-triazole (1.6 g.) in dimethylformamide (20 ml.). After the effervescence had ceased, a solution of 2-(2,4-difluorophenyl)-2,3-epoxy-1-(1,2,4-triazol-1-yl)propane (1.9 g.) in dimethylformamide (10 ml.) was added, and the mixture was heated at 75° C. for 5 hours, then stirred at room temperature for 16 hours. The reaction mixture was diluted with water (150 ml.) and extracted with ethyl acetate (100 ml). The organic layer was washed with water, dried over anhydrous magnesium sulphate and evaporated to dryness. The residue was crystallised from a mixture of ethyl acetate and petroleum ether (b.p. 60°-80° C.) to give 2-[3-(4-cyanostyryl)-1,2,4-triazol-1-yl]-1-(2,4-difluorophenyl)-1-(1,2,4-triazol-1-yl methyl)ethanol, m.p. 189°-91° C.

The 3-(4-cyanostyryl)-1,2,4-triazole used as starting material in the above example may be prepared as follows:

4-Cyanobenzaldehyde (25 g.) and sodium acetate (15.6 g.) were added to acetic anhydride (50 ml.) and heated at 150° C. for 20 hours. The reaction mixture was basified with sodium hydrogen carbonate, then reacidified with 2N hydrochloric acid and extracted with ethyl acetate. The solid material which precipitated on acidification and the ethyl acetate extract were combined and evaporated to give a brown solid (25 g.).

The above solid (12.5 g.) was added to thionyl chloride (50 ml.) and refluxed for 1 hour. The solution was evaporated and the residue was azeotroped with toluene to give a pale brown solid. This was dissolved toluene (50 ml.) and added dropwise to an ice cooled, stirred suspension of thiosemicarbazide (7.1 g.) in pyridine (100 ml.). The mixture was stirred at room temperature for 16 hours, then evaporated to dryness. The residue was dissolved in methanol (100 ml.), treated with a solution of sodium (3.6 g.) in methanol (50 ml.) and stirred and heated under reflux for 16 hours. The reaction mixture was evaporated to dryness, redissolved in water and acidified with 2N hydrochloric acid, and the precipitate was filtered, to give a brown solid which was dried at 100° C.

The solid was added in small portions to a stirred solution of sodium nitrite (0.1 g.) in concentrated nitric acid (15 ml.) in water (30 ml.) at 50° C. Heating was continued for 2 hours, then the reaction mixture was cooled and basified with sodium hydrogen carbonate. The mixture was extracted with ethyl acetate and the extract was dried over anhydrous magnesium sulphate and evaporated, to give 3-(4-cyanostyryl)-1,2,4-triazole and NMR data as follows:

Solvent-DMSO d$^6$—9.5 ppm (singlet, 1H), 7.8 ppm (multiplet, 4H), 7.6 (doublet, 1H), 7.4 (doublet, 1H).

EXAMPLES 5-26

The process described in Example 4 was repeated, using the appropriate substituted triazole in place of 3-(4-cyanostyryl)-1,2,4-triazole and, for Example 26, 2-(5-chloropyridyl)-2,3-epoxy-1-(1,2,4-triazol-1-yl)propane in place of the 2,4-difluorophenyl analogue, to give the following compounds:

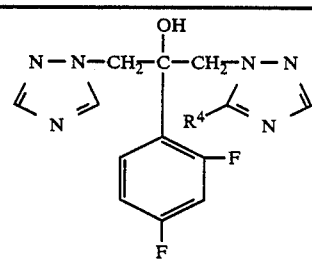

| Example | R$^4$ | M.p. |
|---|---|---|
| 5 | 4-trifluoromethoxystyryl | 130-132 |
| 6 | 4-(2,2,2-trifluoroethoxy)styryl | 117-119 |

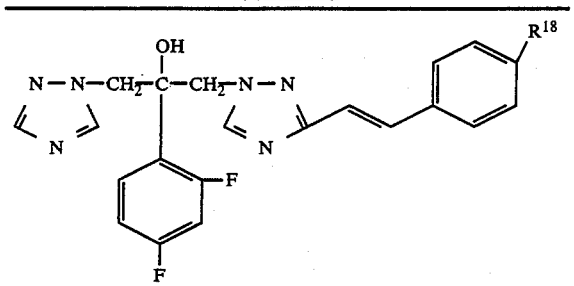

| Example | R[18] | M.p. |
|---|---|---|
| 7 | 1,1,2,2-tetrafluoroethoxy | 130–132 |
| 8 | difluoromethoxy | 128–131 |
| 9 | 2,2,2-trifluoroethoxy | 151–152 |
| 10 | 2-fluoroethoxy | 65–70 |
| 11 | 2,2,3,3-tetrafluoropropoxy | 136–137 |
| 12 | 1-methyl-2,2,2-trifluoroethoxy | 134–135 |
| 13 | 2,2,2-trifluoroethylcarbamoyl | 93(d) |
| 14 | 4-acetylpiperazinylcarbonyl | 80(d) |
| 15 | morpholinocarbonyl | 138 |
| 16 | 4-chlorophenylcarbamoyl | 204–206 |
| 17 | N-methyl-N-(2,2,3,3,4,4,4-heptafluorobutyl)carbamoyl | 112–114 |
| 18 | 2-propynyloxy | 125–130 |
| 19 | cyclopentyloxy | 129–131 |
| 20 | 4-chlorophenoxy | 108–112 |
| 21 | 5-trifluoromethylpyrid-2-yloxy | 91–94 |
| 22 | 1-(methoxycarbonyl)propoxy | 87–89 |
| 23 | 1-carbamoylpropoxy | 150 |
| 24 | 1-carbamoyl-1-methylethoxy | 189–191 |

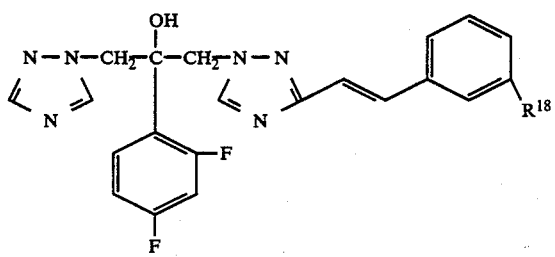

| Example | R[18] | M.p. |
|---|---|---|
| 25 | 4-chlorophenoxy | 105–109 |

OH
N—N—CH₂—C—CH₂—N—N
(structure with pyridine bearing Cl, and styryl-R[18])

| Example | R[18] | M.p. |
|---|---|---|
| 26 | cyano | 136–138 |

Several of the substituted triazoles which are required as starting materials for the synthesis of the above compounds are novel, and were prepared by the process described in the latter part of Example 1, using the appropriate substituted cinnamonitrile in place of 4-trifluoromethoxycinnamonitrile:

| Starting material for Example No. | M.p. | Footnote |
|---|---|---|
| 6 and 9 | 178–180 | 10 |
| 7 | | 11 |
| 8 | | 2, 12 |
| 10 | | 13 |
| 11 | 150–152 | 14 |
| 12 | 95–101 | 14 |
| 13 | | 3, 15 |
| 14 | | 4, 15 |
| 15 | | 5, 15 |
| 16 | | 6, 15 |
| 17 | | 7, 16 |
| 18 | | 8, 17 |
| 19 | 153–155 | 17 |
| 20 | 167–172 | 18 |
| 21 | 161–163 | 19 |
| 22 | 110–111 | 17 |
| 24 | | 9, 20 |
| 25 | 116–117 | 18 |

Footnotes: Nmr data (δ values relative to TMS) in deuteriochloroform. (s = singlet, d = doublet, t = triplet, q = quartet, m = multiplet, b = broad):
1. 8.05 (bs, 1H), 7.6 (m, 4H), 7.2 (d, 2H), 7.05 d, 1H), 6.05 (tt, 1H).
2. 8.38 (bs, 1H), 7.7 (m, 4H), 7.1 (d, 2H), 7.08 d, 1H), 6.3 (t, 1H).
3. 9.1 (t, 1H), 7.9 (d, 2H), 7.8 (d, 2H), 7.6 (d, 1H), 7.3 (d, 1H),
4. 8.1 (s, 1H), 7.4 (m, 5H), 7.0 (d, 1H), 3.5 (m, 4H), 2.1 (s, 3H).
5. 8.1 (s, 1H), 7.6 (s, 1H), 7.45 (d, 2H), 7.4 (d, 2H), 7.4 (d, 2H), 7.3 (d, 1H), 6.9 (d, 1H), 3.7 (m, 1H).
6. 7.3–8.0 (m, 8H), 8.4 (s, 1H).
7. 8.1 (s, 1H), 7.4–7.6 (m, 7H), 7.0 (d, 1H), 4.3 (m, 2H), 4.3 (m, 2H), 3.2 (s, 3H).
8. 8.2 (s, 1H), 7.69–6.82 (m, 6H), 4.76 (d, 2H), 3.46 (t, 1H)
9. Not characterised.
10. The cinnamonitrile required for Examples 6 and 9 was obtained as follows:
A solution of 4-(2,2,2-trifluoroethoxy)benzonitrile (42 g) in toluene (150 ml) was treated, under an atmosphere of argon, with di-isobutylaluminium hydride (280 ml of 1.5 M solution in toluene), over 20 minutes. After a further 25 minutes the reaction mixture was cooled to 0° and a mixture of methanol (80 ml) and toluene (150 ml) was added cautiously, followed by 2 N hydrochloric acid (250 ml). The organic layer was separated, the aqueous layer was extracted twice with ethyl acetate, and the combined organic extracts were washed with water, then dried and evaporated to dryness. The residual oil was 4-(2,2,2-triflouroethoxy)-benzaldehyde; nmr 9.95 (s, 1H), 7.5 (s, 4H), 4.47 (q, 2H). This aldehyde was converted into 4-(2,2,2-trifluoroethoxy)cinnamonitrile by the process described in Example 1.
11. The cinnamontrile required for Example 7 was obtained by the process described in the latter part of Example 1, starting from 4-(1,1,2,2-tetraflouroethoxy)aniline in place of 4-methoxyaniline.
12. The cinnamonitrile required for Example 8 was obtained as follows:
To a solution of 4-hydroxycinnamic acid (20 g) in tetrahydrofan (100 ml) was added to a solution of sodium hydroxide (29.5 g) in water 100 ml). The mixture was heated to 30° with vigorous stirring. Chlorodifluormethane was slowly bubbled through the mixture for 2 hours, then a further solution 29.5 g of sodium hydroxide in water (50 ml) was added, and the addition of gas was continued for a futher 2 hours. The mixture was then cooled to room temperature and water (100 ml) was added, the pH was adjusted with hydrochloric acid to 2 and the mixture was extracted with ethyl acetate (3 × 100 ml). The residue was stirred in chloroform, the solution was filtered and the solvents were evaporated. The residue (3 g) was heated under reflux in methylene chloride, and chlorosulphonyl isocyanate (2 g) was added dropwise. The mixture was heated under reflux for 2 hours, dimethyl formamide (3 ml) was added dropwise, and the mixture was heated under reflux for a further 1 hour. The solution was added to excess aqueous sodium bicarbonate solution, the organic layer was separated and evaporated to dryness, to yield 3.3 g of 4-(difluoromethoxy)cinnamonitrile as a yellow oil, which was used without further purification.
13. The cinnamonitrile for Example 10 was obtained as follows:
4-Hydroxycinnamonitile was alkylated with 2-bromoethanol, by a process analogous to that described below for the preparation of the cinnamonitrile required for Example 24, to give 4-(2-hydroxyethoxy)cinnamonitrile. This compound (45 g) was stirred in a mixture of tetrahydrofuran (20 ml) and chloroform (30 ml) and cooled in acetone/solid carbon dioxide under an atmosphere of argon, and diethylaminosulphur trifluoride (4.9 g) was added from a syringe. The mixture was stirred at room temperature for 24 hours, and poured into a mixture of chloroform and saturated sodium bicarbonate solution. The chloroform extract was separated, washed with water and dried, the solvent was evaporated, and the residue was shown by thin layer chromatography to be 4-(2-fluorethoxy)cinnamonitrile, containing 10–15% of the starting material. This crude product was used without further purification.
14. The cinnamontile required for Examples 11 and 12 were obtained from 4-(2,2,3,3-tetrafluoropropoxy)benzaldehyde and 4-(2,2,2-trifluoro-1-methylethoxy)benzaldehyde respectively, by a similar process to that described above for Examples 6 and 9.
15. The cinnamonitriles required for Examples 13, 14, 15 and 16 were obtained from 2,2,2-trifluoroethylamine, 1-acetylpiperazine, morpholine and 4-chloroaniline respectively by the process described below for obtaining the cinnamonitrile for Example 17.
16. The cinnamonitrile required for Example 17 was obtained as follows:
A solution of diethyl cyanomethylphosphonate (20 g) in dimethoxyethane (20 ml) was added dropwise to a stirred suspension of sodium hydride (6.4 g) in dimethoxyethane (20 ml), the mixture was stirred for 30 minutes, then a solution of 4-carboxybenzaldehyde (20 g) in dimethoxyehtane (30 ml) and dimethylformamide (30 ml) was added dropwise. At the end of the addition, the solution was stirred for 1 hour, then partitioned between ethyl acetate and 2 N hydrochloric acid. The organic extract was separated, washed with water twice and brine twice and dried. The solvent was evaporated, and the residue, which crystallised on trituration with methanol, was 4-carboxycinnamonitrile, mp 286–289°. This acid (5 g) was heated under reflux with thionyl chloride (10 ml) for 3 hours, then evaporated to dryness, and the residue was crystallised from ethyl acetate/hexane, 1:1 by volume, to give 4-choroformylcinnamonitrile, mp 155–157°. This chloroformyl compound (1.2 g) was heated under reflux with chloroform (20 ml) and pyridine (10 ml) for 30 minutes, cooled, and a solution of N-2,2,3,3,4,4,4-heptafluorbutyl)-N-methylamine (1.2 g) in chloroform (10 ml) was added. The mixture was stirred for 1 hour. the solvent was evaporated, and the residue was partitioned between ethyl acetate and water. The organic layer was separated, washed twice with 2 N hydrochloric acid, twice with water and twice with brine, and dried. The solvent was evaporated, and the residue, 4-[N-(2,2,3,3,4,4,4-heptafluorobutyl)-N-methylcarbamoyl]cinnamonitrile had nmr 7.6–7.4 (m, 5H), 6.0 (d, 1H), 4.3 (m, 2H), 3.1 (s, 1H), and was used without further purification.
17. The cinnamonitriles required for Examples 18, 19 and 22 were obtained from propargyl bromide, cyclopentyl bromide and methyl 1-bromobutyrate respectively, by a similar process to that described below for Example 24.
18. The cinnamonitrile required for Example 20 was obtained as follows:
Diethyl cyanmethylphophonate (125 g) was added over 20 minutes to a stirred suspension of sodium hydride (3.5 g of a 57% dispersion, washed oil-free) in tetrahydrofuran (75 ml) and dimethylformamide (25 ml) under an atmosphere of argon, below 5°. A solution of 4-(4-chlorophenoxy)benzaldehyde (16.2 g) in tetrahydrofuran (15 ml) was added over 3 minutes, and the reaction mixture was left at room temperature overnight. It was then poured into ethyl acetate and water, the organic layer was separated, washed with brine and dried, and the solvent was evaporated. The residue was purified by medium pressure liquid chromatography to give 4-(4-chlorophenoxy)-cinnamonitrile, nmr 7.75 (d, 1H) 7.28 (m, 4H), 6.92 (m, 4H), 5.70 (d, 2H).
The cinnamonitrile for Example 25 was prepared similarly, using 3-(4-chlorophenoxy)benzaldehyde.
19. The cinnamonitrile required for Example 21 was obtained as follows:
2-Fluoro-5-trifluormethylpyridine (115 g) and solid potassium salt of p-hydoxybenzaldehyde (105 g Suter et al, J. Amer. Chem Soc 53, 1567, (1931)) were stirred in dimethylsulphoxide (100 ml) at 80–90° for 6 hours. The reaction mixture was cooled and partitioned between methylene chloride and water. The organic layer was separated, washed successively with 0.1 N sodium hydroxide solution (three times), dilute hydrochloric acid and brine, and dried. The solvent was evaporated, and the residue crystallised on cooling in absolute ethanol for 20 hours, to give 4-(5-trifluoromethylpyrid-2-yloxy)benzaldehyde, m.p. 31–33°. This benzaldehyde was converted to the corresponding cinnamonitrile by the process described in the latter part of Example 1.
20. The cinnamonitrile required for Example 24 was obtained as follows:
A solution of sodium hydride (0.9 g of a 50–55% suspension, washed free of oil with 60–80° petrol) in N-methylpyrrolidone (20 ml) was treated with a solution of 4-hydroxycinnamonitrile (2.9 g) in N-methylpyrrolidone (20 ml). After stirring for 10 minutes, 1-bromo-1-methylpropionamide (4.15 g) was added in one portion, the solution was stirred at room temperature for 3½ hours, poured into water and extracted three times with ethyl acetate. The extracts were combined, washed with 2.5 N sodium hydroxide solution twice and water twice and dried. Evaporation cinnamonitrile as a white solid, mp 128–30°.

The 3-[4-(1-carbamoylpropoxystyryl]-1,2,4-triazole used in the manufacture of the compound of Example 23 was prepared as follows:

3-[4-(1-methoxycarbonylpropoxy)styryl]-1,2,4-triazole (0.5 g—prepared as the intermediate for Example 22 above), concentrated ammonia (5 ml) and ethanol (10 ml) were placed in a Carius tube, and further saturated with gaseous ammonia for 20 minutes. The tube was cooled in acetone/solid carbon dioxide and sealed, and then heated at 110° for 24 hours. The tube was cooled and opened, and the contents were evaporated to dryness to give the required 3-[4-(1-carbamoylpropoxy)styryl]-1,2,4-triazole, crystallised from methanol, softened at 50° and mp~150°.

EXAMPLES 27–35

The process described in Example 1 was repeated, using the appropriate substituted triazole in place of 3-(4-trifluoromethoxystyryl)-1,2,4-triazole, and the appropriate ketone in place of 2,4-difluoroalpha-(1,2,4-triazol-1-yl)acetophenone, to give following compounds:

| Example | $R^{19}$ | $R^{20}$ | Z | $R^{21}$ | M.p. |
|---|---|---|---|---|---|
| 27 | Cl | Cl | CH | $OCF_3$ | 159–161 |

-continued

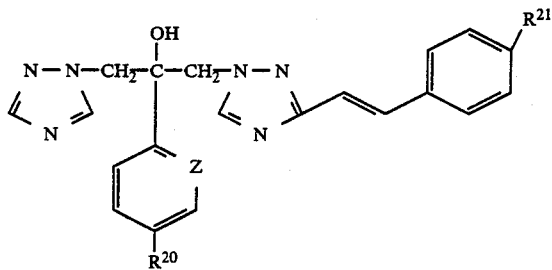

| Example | R[19] | R[20] | Z | R[21] | M.p. |
|---|---|---|---|---|---|
| 28 | H | Cl | N | OCH$_2$CF$_3$ | 138–140 |
| 29 | H | CN | CH | CF$_3$ | 212–213 |
| 30 | H | CN | CH | Cl | 228–230 |
| 31 | H | CN | CH | F | 252–254 |
| 32 | H | CN | CH | Br | 208–210 |
| 33 | F | F | CH | NO$_2$ | 112–115 |

Several of the substituted triazoles which are required as starting material for the synthesis of the above compounds are novel, and were prepared by the process described in the latter part of Example 1, using the appropriate substituted cinnamonitrile in place of 4-trifluoromethoxycinnamonitrile:

| Starting material for Example No. | M.p. | Footnote |
|---|---|---|
| 29 | 141–143 | |
| 28 | 178–180 | |
| 30 | 178–182 | |
| 31 | 140–143 | |
| 32 | 213–214 | |
| 33 | | 1 |

Footnote
1. Nmr in d$_6$-DMSO: δ 8.1 (m, 4 H), 7.7 (d, 1 H), 7.4 (d, 1 H).

The 2,4-dichlorophenyl-alpha-(1,2,4-triazole-1-yl)acetophenone used as the starting material in Example 27 was prepared as follows:

Alpha, 2,4-trichloroacetophenone (20 g) was dissolved in acetonitrile (25 ml) and added dropwise to a refluxing solution of 1,2,4-triazole (6.2 g) and potassium carbonate 13.4) in acetonitrile (25 ml). When the addition was complete, the solution was allowed to cool and was stirred for 2 hours. The solvent was evaporated and the residue was partitioned between ethyl acetate and water. The ethyl acetate layer was separated, washed twice with water and twice with brine, dried over sodium sulphate and filtered. The filtrate was evaporated to dryness under reduced pressure, and the residue was chromatographed on a K60 silica column, eluting with ethyl acetate, to give 2,4-dichloro-alpha-(1,2,4-triazol-1-yl)acetophenone, which when crystallised from ethyl acetate/petroleum ether (b.p. 60°–80°), had m.p. 116°–117°.

The 4-cyano-alpha-(1,2,4-triazol-1-yl)acetophenone used as a staring material in Examples 30–33 was prepared as follows:

A solution of bromine (110 g) in chloroform (20 ml) was added dropwise to a stirred solution of 4-cyanoacetophenone (10.0 g) in chloroform (90 ml). When the addition was complete, the solution was stirred for 0.5 hour, washed twice with water, twice with sodium bicarbonate solution and dried. The solvent was evaporated under reduced pressure, and the residue was alpha-bromo-4-cyanoacetophenone; nmr in deuteriochloroform: 8.2 (d, 2H), 7.8 (d, 2H), 4.7 (s, 2H).

1,2,4-Triazole (9.2 g) and potassium carbonate (18.5 g) were suspended in anhydrous acetone (60 ml), cooled in ice and stirred, while a solution of alpha-bromo-4-cyanoacetophenone (10.0 g) in anhydrous acetone (80 ml) was added. After the addition was complete, the solution was stirred, in ice, for a further 0.5 hours, then poured into 0.1M hydrochloric acid (600 ml) and extracted with ethyl acetate. The extracts were combined, washed with water twice and brine twice dried and filtered, and the filtrate was evaporated to dryness. The residue was purified by chromatography on a K60 silica column, eluting with mixtures of chloroform and methanol, 95:5, 90:10 and 50:50 by volume, to give the required starting material, 4-cyano-alpha-(1,2,4-triazol-1-yl)acetophenone, crystallised from ethyl acetate m.p. 210°–214°.

EXAMPLE 34

1-(2,4-Difluorophenyl)-2-[3-(4-hydroxystyryl)-1,2,4-triazol-1-yl]-1-(1,2,4-triazol-1-ylmethyl)ethanol (710 mg) was dissolved in N-methylpyrrolidone (10 ml., dried over molecular sieve), and sodium hydride (57% dispersion in oil, 75 mg) was added in portions. When the evolution of hydrogen had ceased, p-chlorobenzyl chloride (300 mg) was added, and the mixture was stirred at 80° for 3 hours and then for 18 hours at room temperature. The reaction mixture was poured into 0.1N hydrochloric acid and extracted with ethyl acetate. The extracts were combined, washed successively with water, 0.5N sodium hydroxide solution (twice), water and brine, and was then filtered through anhydrous sodium sulphate. The filtrate was evaporated, and the crude product was purified by medium pressure liquid chromatography, eluting with chloroform, to give 2-[3-(4-p-chlorobenzyloxystyryl)-1,2,4-triazol-1-yl]-1-(2,4-difluorophenyl)-1-(1,2,4-triazol-1-ylmethyl)ethanol, crystallised from diethylether/ethyl acetate/petroleum ether, m.p. 103°–106°.

The 4-hydroxystyryl starting material used in the above process may be obtained as follows:

The process described in the latter part of Example 1 was repeated, using 4-methoxycinnamonitrile in place of 4-trifluoromethoxycinnamonitrile, to give 3-(4-methoxystyryl)-1,2,4-triazole. The process described in the first part of Example 1 was then repeated, using this 3-(4-methoxystyryl)-1,2,4-triazole in place of 3-(4-trifluoromethoxystyryl)1,2,4-triazole to give 1-(2,4-difluorophenyl)-2-[3-(4-methoxystyryl)-1,2,4-triazol-1-yl]-1-(1,2,4-triazol-1-ylmethyl)ethanol, m.p. 150°–152°.

This product (3.3 g) was dissolved in glacial acetic acid (75 ml), 48% hydrobromic acid (75 ml) was added, and the mixture was heated under reflux, in an atmosphere of argon, for 2 hours. The solvents were evaporated under reduced pressure, the residue was taken up in chloroform (400 ml) and water (50 ml), and the mixture made to pH7 by the addition of solid sodium bicarbonate. The organic layer was separated and filtered through solid anhydrous sodium sulphate. The neutralised reaction mixture was similarly extracted a second time with chloroform. The chloroform extracts were combined and evaporated to dryness to give the required 4-hydroxystyryl starting material; nmr in deuteriochloroform: 8.35 (s, 1H), 8.25 (s, 1H), 7.72 (s, 1H), 7.5–6.6 (m, 9H), 5.8 (bs, 1H), 4.9–4.6 (m, 4H).

EXAMPLE 35

The process described in Example 34 was repeated, using 2-bromoethanol in place of p-chlorobenzyl chloride, to give 1-(2,4-difluorophenyl)-2-[3-(4-[hydroxyethoxy]styryl)-1,2,4-triazol-1-yl]-1-(1,2,4-triazol-1-ylmethyl)ethanol, m.p. 152°–155°.

EXAMPLE 36

A solution of 2-(2,4-difluorophenyl)-2,3-epoxy-1-[3-(4-trifluoromethoxystyryl)-1,2,4-triazol-1-yl]propane (3.13 g) in dimethylformamide was treated with triazole (0.85 g) and heated on a steam bath for 2.5 hours. The reaction mixture was poured into water and extracted with ethyl acetate, and the extracts were combined, washed with water dried over sodium sulphate and evaporated to dryness. The residue was purified by column chromatography on silica, eluting with ethyl acetate:methanol, 95:5 by volume, and the oil crystallised from ethyl acetate/hexane to give 1-(2,4-difluorophenyl)-2-[2-[3-(4-trifluoromethoxystyryl)-1,2,4-triazol-1-yl]-1-(1,2,4-triazol-1-ylmethyl)ethanol, m.p. 151°–153°, identical with the product obtained in Example 1.

The epoxy-propane starting material used in the above process, was obtained as follows:

Sodium hydride (2.05 g of a 55% dispersion in oil) was washed oil-free with petroleum ether, b.p. 60°–80°, and suspended in acetonitrile, and to the suspension was added, in portions over 10 minutes, 3-(4-trifluoromethoxystyryl)-1,2,4-triazole (10.88 g), prepared as described in Example 1. The mixture was stirred for 20 minutes and cooled to 0°, and then a solution of alpha-bromo-2,4-difluoroacetophenone (20 g) in acetonitrile (35 ml) was added over 15 minutes. The resulting solution was allowed to warm to room temperature, and stirred for 18 hours, then was poured in 0.15M hydrochloric acid and extracted with ethyl acetate. The extracts were combined, washed with water, dried over sodium sulphate and evaporated to dryness. The residue solified on standing, and was crystallised from isopropanol to give 2,4-difluoro-alpha-[3-(4-trifluoromethylstyryl)-1,2,4-triazol-1-yl]acetophenone, m.p. 127°–135°.

Sodium hydride (0.38 g of a 55% dispersion in oil) was washed oil-free with petroleum ether, b.p. 60°–80° and suspended in dry dimethylformamide (25 ml) under an atmosphere of argon. Trimethyl oxosulphonium iodide (2.19 g) was added, and after the evolution of hydrogen had ceased, the mixture was stirred for 0.5 hour, then a solution of the above-described acetophenone (2.6 g) in dry dimethylformamide (12 ml) was added. The reaction mixture was heated at 55° for 1.25 hours, then poured into water and extracted with ethyl acetate. The combined extracts were washed with water, dried and evaporated to dryness to give the required epoxy-propane starting material as a light brown oil, which was used without further purification.

EXAMPLE 37

A mixture of 1-(2,4-difluorophenyl)-2-(3-formyl-1,2,4-triazol-1-yl)-1-(1,2,4-triazol-1-ylmethyl)ethanol (0.6 g), p-methoxybenzyl-triphenylphosphonium chloride (1.68 g), potassium carbonate (0.5 g) and methanol (10 ml) was heated at 60°–70° for 2 hours, then left at room temperature for 20 hours. The reaction mixture was filtered, the separated solids were washed with methanol, and the combined organic solutions were evaporated to dryness. The residue was purified by medium pressure liquid chromatography on silica, eluting with chloroform, to give 1-(2,4-difluorophenyl)-2-[3-(4-methoxystyryl)-1,2,4-triazol-1-yl]-1-(1,2,4-triazol-1-ylmethyl)ethanol, m.p. 150°–152°.

The 1-(2,4-difluorophenyl)-2-(3-formyl-1,2,4-triazol-1-yl)-1-(1,2,4-triazol-1-ylmethyl)ethanol used as starting material in the above process may be obtained as follows:

Sodium hydride (1.4 g of 55% dispersion in oil) was washed oil-free with cyclohexane, and suspended in dry N-methylpyrrolidone. A solution of 3-diethoxymethyl-1,2,4-triazole (Browne, Australian J. Chemistry, 1971, 24, 393), (5.0 g), in dry N-methylpyrrolidone (25 ml) was added by syringe to the stirred sodium hydride suspension, and after the addition, when gas evolution had ceased, a solution of 2-(2,4-difluorophenyl)-2,3-epoxy-1-(1,2,4-triazol-1-yl)propane (8.2 g) in N-methylpyrrolidone (50 ml) was added, and the reaction mixture was heated to 70° for 2 hours. The reaction mixture was poured into water (800 ml) and extracted with ethyl acetate (3×200 ml). The extracts were combined, the solvent was evaporated, and the residue was purified by medium pressure liquid chromatography on silica, eluting with chloroform, to give 2-(3-diethoxymethyl-1,2,4-triazol-1-ylmethyl)-1-(2,4-difluorophenyl)-1-(1,2,4-triazol-1-yl)ethanol, m.p. 107°–108°.

This product (2.0 g) was dissolved in 2N hydrochloric acid (25 ml) and stirred for 16 hours at room temperature, then neutralised with solid sodium bicarbonate and extracted with ethyl acetate (3×50 ml). The extracts were combined and dried, and the solvent was evaporated to give an oil which crystallised on trituration with anhydrous diethyl ether to give the required starting material, m.p. 85°–87°.

$$A^1.CH_2CR(OH)CH_2.A^2 \qquad \text{I}$$

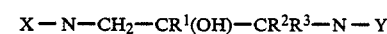

II

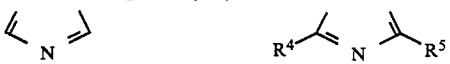

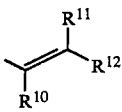

III

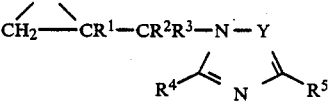

IV

V

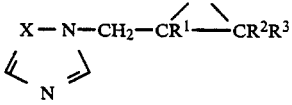

VI

HN—Y

VII

-continued

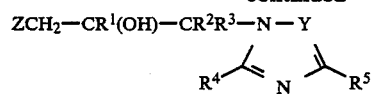

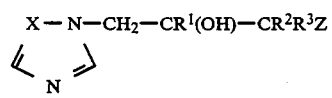

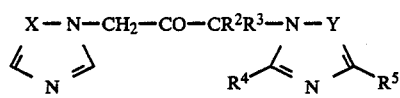

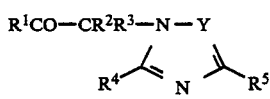

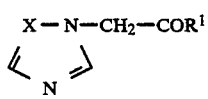

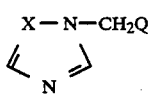

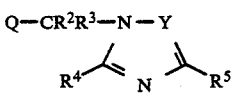

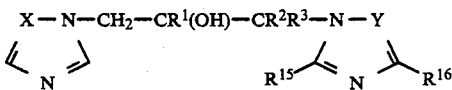

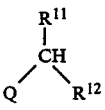   R$^{11}$CH—R$^{12}$   Q

R$^{17}$CN   XVII

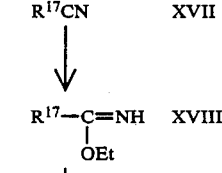

HN—N   XIX

R$^1$CO.CHR$^2$R$^3$   XXI

R$^1$CO.CR$^2$R$^3$Br   XX

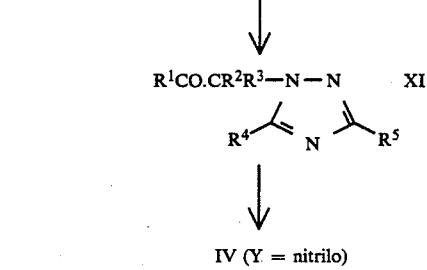

IV (Y = nitrilo)

-continued

VIII   NC.CH$_2$CO$_2$Et + R$^1$MgI ⟶ R$^5$CO.CH$_2$CO$_2$Et
      XXII       XXIII

IX

R$^5$CO.CH(NH$_2$)CO$_2$Et ⟵ R$^5$CO.C(:NOH)CO$_2$Et
     XXV       XXIV

X

XI 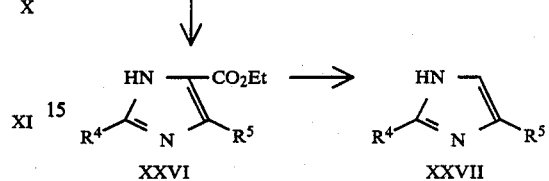

XII   NC.CH$_2$CO$_2$Me + R$^5$CN ⟶ 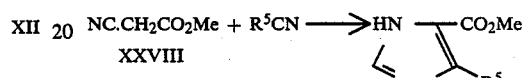
     XXVIII

XIII

XIV 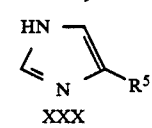

XV   XXXI   R$^1$COCH$_3$ ⟶ R$^1$COCH$_2$Br   XXXII

XVI

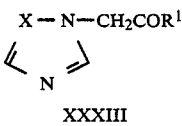

R$^2$R$^3$CH.Q
XXXIV

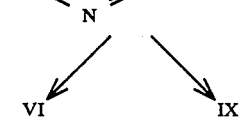

↓      ↓
VI      IX

What we claim is:
1. A compound of the formula:

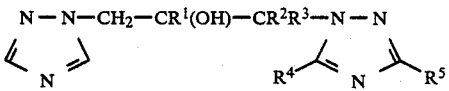

wherein:
R' is phenyl bearing one or more substituents selected from the group consisting of halogen and cyano;

$R^2$ and $R^3$, which may be the same or different, are each hydrogen or a 1-6C alkyl radical;

one of $R^4$ and $R^5$ is hydrogen and the other is a styryl radical substituted in the phenyl ring by one or more substituents selected from the group consisting of:

halogen atoms;

cyano, nitro, and 1-6C alkoxy, halogenoalkyl and halogenoalkoxy radicals;

provided that $R^1$ is a phenyl radical bearing at least one cyano substituent, or at least one of $R^4$ and $R^5$ is a styryl radical, substituted in the phenyl ring thereof by at least one substituent selected from cyano, nitro and 1-6C halogenoalkoxy or an acid addition salt of those compounds which contain a basic substituent.

2. A compound as claimed in claim 1 wherein $R^1$ is a fluorophenyl radical, $R^4$ is hydrogen and $R^5$ is a styryl radical substituted in the phenyl ring by a cyano, 1-4C alkoxy bearing 1 to 4 fluorine substituents.

3. A compound as claimed in claim 2 wherein $R^1$ is 2,4-difluorophenyl, $R^4$ is hydrogen and $R^5$ is a 4-(difluoromethoxy)styryl, trifluoromethoxystyryl, 4-(2,2,2-trifluoroethoxy)styryl, 4-(1,1,2,2-tetrafluoroethoxy)styryl, 4-(2,2,3,3-tetrafluoropropoxy)styryl, 4-(1-methyl-2,2,2-trifluoroethoxy)styryl, 4-cyanostyryl.

4. A pharmaceutical or veterinary antifungal composition comprising an antifungally effective amount of a compound as claimed in claim 1 together with a pharmaceutically or veterinarily acceptable diluent or carrier.

5. A plant antifungal composition comprising an antifungally effective amount of a compound as claimed in claim 1 together with a non-pharmaceutical diluent or carrier.

6. A method of combatting fungal diseases in a plant, which comprises applying to the plant, or to the locus of the plant, an antifungally effective amount of a compound as claimed in claim 1.

7. A method of treating a fungal infection in an animal host which comprises administering to said host an antifungally effective amount of a compound as claimed in claim 1.

* * * * *